United States Patent [19]

Van Heuvelen

[11] Patent Number: 4,704,029

[45] Date of Patent: Nov. 3, 1987

[54] BLOOD GLUCOSE MONITOR

[75] Inventor: Alan Van Heuvelen, Las Cruces, N. Mex.

[73] Assignee: Research Corporation, New York, N.Y.

[21] Appl. No.: 813,742

[22] Filed: Dec. 26, 1985

[51] Int. Cl.[4] ............................................. G01N 33/16
[52] U.S. Cl. ....................................... 356/39; 128/633; 356/136; 436/95
[58] Field of Search ................. 356/39, 135, 136, 137, 356/344; 128/633; 422/68; 436/95

[56] References Cited

U.S. PATENT DOCUMENTS

| 3,449,051 | 6/1969 | Levitt | 356/135 |
| 3,902,807 | 9/1975 | Fleming et al. | 356/51 |
| 4,169,676 | 10/1979 | Kaiser | 356/39 |
| 4,451,147 | 5/1984 | Dobes et al. | 356/135 |

FOREIGN PATENT DOCUMENTS 40187  3/1977  Japan .................................. 356/136

Primary Examiner—R. A. Rosenberger
Attorney, Agent, or Firm—Scully, Scott, Murphy & Presser

[57] ABSTRACT

A blood glucose monitor which is particularly applicable for use as an implant for controlling an insulin pump, or as a portable device for use by a diabetic for home blood glucose monitoring. The glucose monitor measures the glucose level of blood by utilizing a refractometer which measures the index of refraction of blood adjacent to an interface with a transparent surface of the refractometer, by directing light at the interface to measure the index of refraction of the blood by the amount of radiation reflected by the interface, particularly light incident near the critical angle. In a preferred embodiment, polarized light is directed against an interface in an implant between a transparent material and the blood. As the glucose concentration in the blood changes, its index of refraction changes, as does the intensity of light reflected from the interface. The angle of incidence of the light is selected to be slightly less than the critical angle for total internal reflection, with the result that the reflected intensity varies dramatically with index of refraction and with glucose concentration. A differential amplifier compares the intensity of the light reflected from the blood and the intensity of the beam before reflection. The output signal from the differential amplifier indicates only a change in the intensity of the reflected light caused by a change in the glucose concentration from a standard setting.

13 Claims, 9 Drawing Figures

BLOOD GLUCOSE MONITOR

BACKGROUND OF THE INVENTION

1. Field of the Invention

The present invention relates generally to a blood glucose monitoring method and device, and more particularly pertains to such a blood glucose monitor which can be constructed as an implant or as a portable device for blood glucose monitoring by a diabetic. As an implant, the glucose concentration in blood adjacent to the implant is measured, such that it is particularly useful for controlling an insulin pump for a diabetic person. The teachings of the present invention can also be used in the construction of a portable device useful for home blood glucose monitoring by diabetics in which the concentration of glucose in a drop of capillary blood is measured.

2. Discussion of the Prior Art

There are about one million insulin-dependent (Type I) diabetics in the United States. The vast majority treat their diabetes by regulating diet and exercise, and by taking one or more shots of insulin each day. Because of the many variations in life and in some cases the lack of dedication to maintaining tight control, blood glucose levels often fluctuate radically, and are responsible for a myriad of complications of the vascular and nervous systems.

Insulin pumps are a recent innovation that are gaining popularity in the treatment of diabetes. These pumps are now used by over ten thousand diabetics. Approximately one hundred of the pumps have been implanted (the majority in Germany), whereas the others are worn outside the body. Most of these pumps emit insulin continuously (twenty four hours a day) at a low-dosage (basal) rate. Before meals, the rate of insulin pumping is increased to a high dosage (bolus) rate to help metabolize food eaten during the meal. The high dosage supplement can be adjusted by the user, whereas the basal pumping rate is usually not adjusted unless a physician is consulted.

Considerable effort and money have been expended to develop a blood glucose monitoring device which automatically adjusts the rate of insulin pumping based upon the varying need of the body for insulin. This need can change dramatically from day to day and at different times within a day, depending on the level of activity and general physical and mental health of the diabetic.

Most efforts at building an implantable blood glucose monitoring device have centered on the use of a glucose oxidase enzyme electrode that measures the interaction of glucose in the blood with the enzyme glucose oxidase. These electrodes are specific for glucose and work well for several days, but deteriorate rather quickly as the enzyme becomes denatured and as antibodies and proteins in the blood clog the active working surface thereof.

The patent literature also discloses many inventions for glucose measuring instruments and implants. For instance, March U.S. Pat. No. 3,958,560 discloses a glucose sensor which utilizes a measurement of radiation through the cornea of the eye. March U.S. Pat. No. 4,014,321 is similar to the preceeding patent, but uses two frequencies of polarized radiation, and measures the optical rotation thereof. Edelman U.S. Pat. No. 4,073,292 discloses an implant which injects Benedict's solution to react with urine from kidney, and measures the transmittance of light from an LED to a photodetector, and thereby controls the insulin injection. Rao, et al. U.S. Pat. No. 4,140,963 discloses an implant with an electrochemical glucose cell, which may be of many different types to produce an electrical measurement signal.

The patent literature also dicloses many optical instruments having technical optical approaches similar to the present invention, but not involved in the measurement of blood glucose levels. For instance, Barnes U.S. Pat. No. 2,413,208 discloses a refractometer with a differential optical system, in which a prism has one surface adjacent to a liquid sample being measured and a second surface adjacent to a reference liquid, and the instrument operates at an angle just below the critical angle to enhance its sensitivity. Rando U.S. Pat. No. 3,450,476 also discloses an interferometer for measuring the index of refraction of a sample. Lubbers U.S. Pat. No. 4,306,877 discloses an instrument in which an indicator behind a permeable membrane reacts to monochromatic radiation, as by a change of color, to indicate the concentration of a substance of interest.

However, the prior art does not disclose a technical approach for measuring the level of glucose in blood similar to that of the present invention, which is suitable for construction as an implant or probe, such that it can be used for controlling an insulin pump, or as a portable device for home blood glucose monitoring.

SUMMARY OF THE INVENTION

Accordingly, it is a primary object of the present invention to provide a blood glucose monitor which is particularly applicable for use in controlling an insulin pump for a diabetic person or as a portable device for home blood glucose monitoring.

A further object of the subject invention is the provision of a blood glucose monitor as described which can be constructed as an implant, and will not deteriorate in a short period of time similar to prior art glucose oxidase enzyme electrodes.

In accordance with the teachings herein, the present invention provides an improved glucose monitor which measures the glucose level of blood by utilizing a refractometer which measures the index of refraction of blood at an interface with a transparent surface of the refractometer, by directing light or infrared radiation (IR) at the interface to measure the index of refraction of the blood by the amount of radiation reflected and refracted by the interface, particularly light or IR incident near the critical angle.

In a preferred embodiment of the present invention, polarized light or IR is directed against an interface between a transparent material and the blood. As the glucose concentration in the blood changes, its index of refraction changes, as does the intensity of light reflected from the interface. The angle of incidence of the light is selected to be slightly less than the critical angle for total internal reflection, with the result that the reflected intensity varies dramatically with changes in the index of refraction caused by changes in glucose concentration. A differential amplifier improves sensitivity by comparing the intensity of the light reflected from the blood with the intensity of the beam before reflection. The output voltage signal from the differential amplifier indicates only a change in the intensity of the reflected light caused by a change in the glucose concentration from a standard setting.

One important aspect of the measurement technique of the present invention is the reliance on the dramatic variation of the intensity of transverse polarized light reflected from an interface between the blood and a transparent material.

An implant pursuant to the present invention is designed to directly contact the blood, and the contacting material of the interface is preferably constructed of a material having an appropriate critical surface tension, which should be much less susceptible to deterioration by antibodies and proteins. One such exemplary material is dichloro-dimethyl-silane, also known as G.E. Dry Film.

The present invention is quite accurate, and experiments indicate that it allows glucose concentrations to be measured with an accuracy of approximately $\pm 10$ mg/dl over a range from about 30 mg/dl to 300 mg/dl, (the normal range in humans is 80–120 mg/dl). By using an instrument with multiple reflections of the polarized light beam therein, even better accuracy should be attainable.

BRIEF DESCRIPTION OF THE DRAWINGS

The foregoing objects and advantages of the present invention for a blood glucose monitor may be more readily understood by one skilled in the art, with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
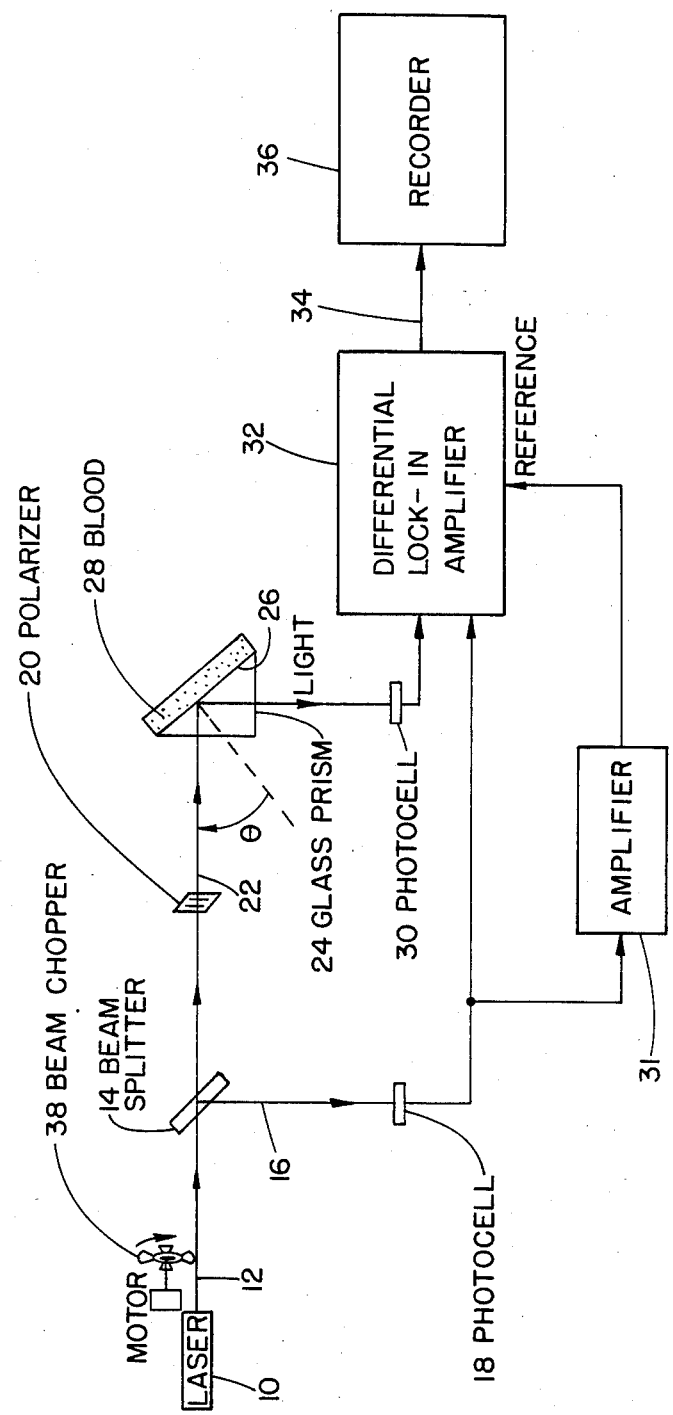
FIG. 1 is a schematic illustration of an exemplary embodiment of a blood glucose monitor constructed pursuant to the teachings of the present invention and illustrating the broad principles of operation thereof.

Referring to the drawings in detail, FIG. 1 is a schematic illustration of an exemplary embodiment of a blood glucose monitor constructed pursuant to the teachings of the present invention, and illustrates the general principles of operation thereof. A laser 10 generates a beam of radiation 12 which, after passing through a modulating beam chopper 38 provided for noise suppression, is incident upon a beam splitter 14, which reflects a portion of the beam to establish a reference beam 16, the intensity of which is measured by a detector 18. The portion of the beam 12 which passes through the beam splitter is incident upon a polarizing filter 20 to produce a beam of transverse polarized light 22, which is directed through a prism 24 to an optical interface 26 formed by one face of the prism which is in direct contact with the blood 28 being monitored.

A portion of the incident polarized beam is reflected by the optical interface 26 onto a measuring detector 30, and a portion of the incident polarized beam is refracted at the optical interface 26 onto the blood. The portion reflected/refracted radiation depends upon the index of refraction of the prism $n_1$, the index of refraction of the blood $n_2$, and the angle of incidence $\theta$ of the incident beam relative to the interface.

Figure 2:
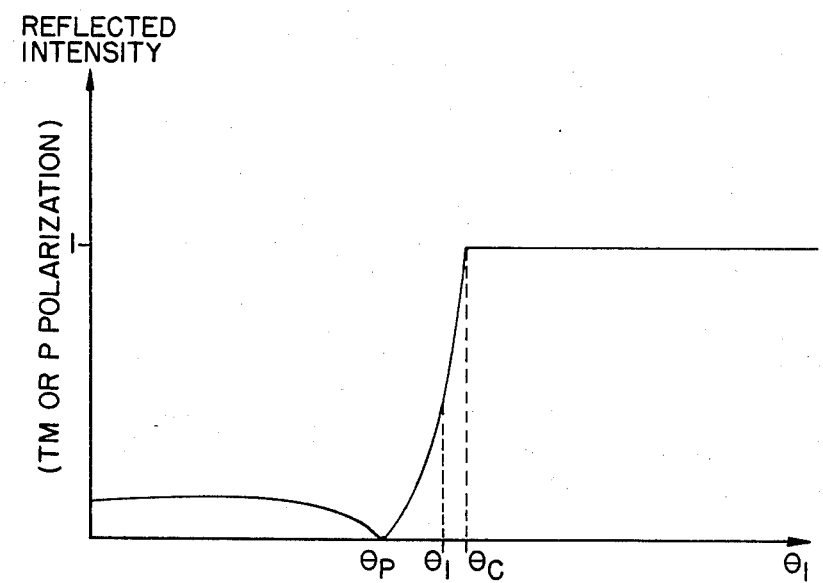
FIG. 2 illustrates a curve of reflected radiation versus angle of incidence, and illustrates the dramatic change thereof at operation near the critical angle of incidence.

FIG. 2 illustrates a curve of reflected radiation versus angle of incidence, and illustrates the dramatic change thereof at operation near the critical angle $\theta_c$. Radiation at low angles of incidence is mainly refracted into the blood sample until the principal angle $\theta_p$ is reached, after which the proportion of radiation reflected by the interface rises dramatically until the critical angle $\theta_c$ is reached, after which total reflection occurs. The curve of FIG. 2 is also illustrative of the fraction of Transverse Magnetic (TM) polarized light reflected from a glass-blood interface, plotted as a function of angle $\theta$. When the interface is oriented at a fixed angle slightly less than the critical angle and the blood glucose (BG) concentration changes, the index of refraction of the blood changes, as does the critical angle. Thus, the curve, in effect, moves slightly left (low BG) or right (high BG). The intensity of the reflected light changes significantly if on the steep part of the reflection curve.

In an arrangement similar to that of FIG. 1 wherein an optical interface between materials having indices of refraction $n_1$ and $n_2$ reflects a beam incident at angle $\theta_c$, $$\theta_c = \sin(-1 n_2/n_1)$$

$\theta_c$ changes as $n_2$ changes $$\theta_c = \sin(-1 n_2/n_1) \text{ (glucose concentration changes)}$$

Thus, the portion of light reflected by the interface in the arrangement of FIG. 1 is dependent upon the angle of incidence of the radiation beam at the interface, the index of refraction $n_1$ of the prism at the interface, and the index of refraction $n_2$ of blood at the interface. As illustrated by FIG. 2, the instrument is very sensitive when operated at an angle of incidence $\theta$ just below the critical angle. In a fixed arrangement as illustrated in FIG. 1, only $n_2$ will vary, and thus the intensity of the radiation detected by 30 is a measurement of $n_2$.

In the arrangement of FIG. 1, a differential amplifier 32 improves sensitivity by comparing the intensity of the light reflected from the blood as measured by detector 30 with the intensity of the reference beam before reflection as measured by detector 18. The output signal 34 from the differential amplifier, which is recorded at 36, indicates only a change in the intensity of the reflected light caused by a change in the glucose concentration from a standard setting. Noise and sensitivity is further improved in this embodiment by the beam modulator or chopper 38 and an amplifier 31 for the reference photocell 18 that provides a reference frequency signal for the differential lock-in amplifier 32.

Figure 7:
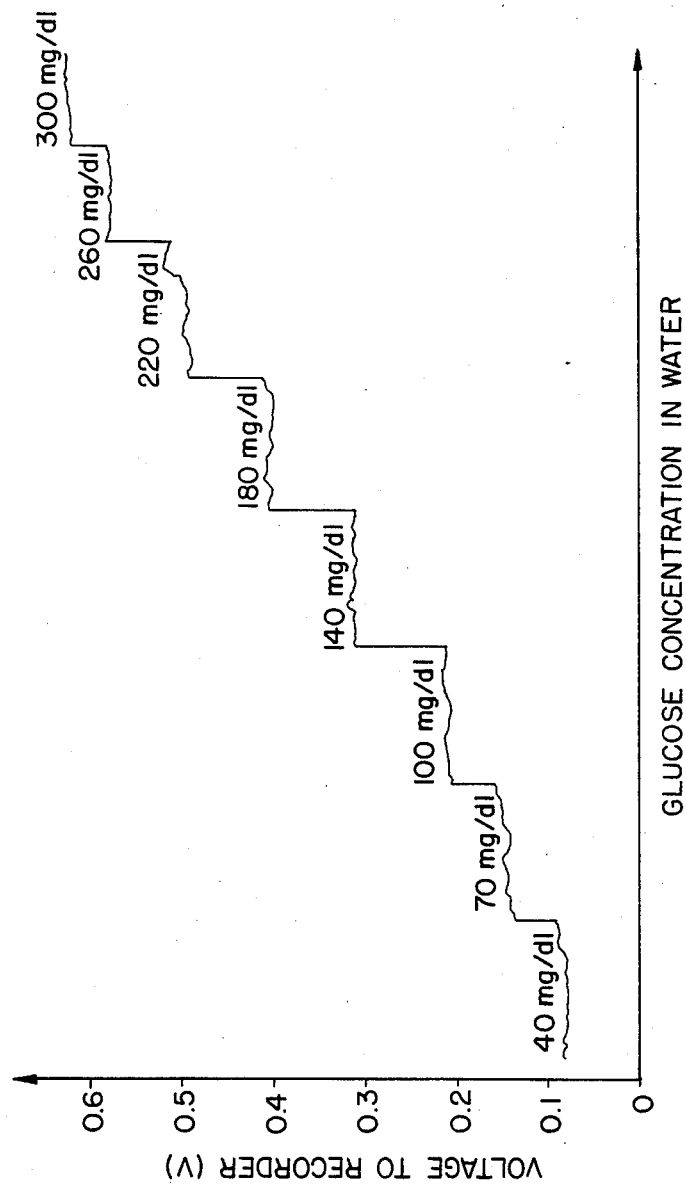
FIG. 7 is a graph obtained with an arrangement similar to that illustrated in FIG. 1, showing the variation of the recorder output with varying glucose concentrations in water.
Figure 8:
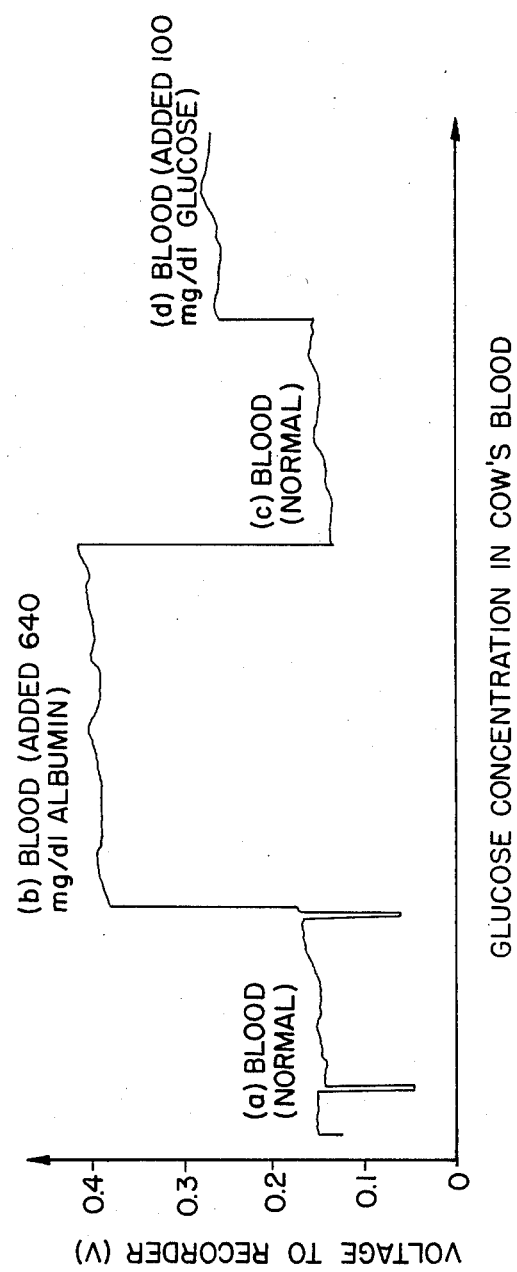
FIG. 8 is a graph obtained with an arrangement similar to that illustrated in FIG. 1, based on cow blood with varying concentrations of glucose therein.

FIGS. 7 and 8 illustrate signals obtained by an arrangement similar to that illustrated in FIG. 1 with varying glucose concentrations in water and in cow's blood.

FIG. 7 is a graph obtained with an arrangement similar to that illustrated in FIG. 1, showing the variation of the recorder output with varying glucose concentrations in water, and FIG. 8 is a graph obtained also with an arrangement similar to that illustrated in FIG. 1, based on cow blood with varying concentrations of glucose therein. Referring to FIG. 8, recorder voltages (a) and (c) represent cow blood with normal glucose concentration, (b) cow blood to which 640 mg/dl albumin was added, and (d) cow blood to which 100 mg/dl glucose was added.

Unfortunately, the arrangement of FIG. 1 is not specific for glucose alone, and many measurements with an arrangement similar to that of FIG. 1 have been made using cow blood with other concentrations of glucose, albumin, urea nitrogen, uric acid, cholesterol, and sodium chloride. Only the glucose and albumin produced observable voltage changes at physiological concentrations. Of all other blood constituents tested (urea nitrogen, uric acid, cholesterol, albumin, and sodium chloride), only albumin produced a signal having variations similar to those caused by variations in glucose. A variation of albumin concentration of 300 mg/dl (8 percent) causes about the same response in the apparatus as a variation in glucose concentration of 100 mg/dl. Since albumin does vary by about this much in normal blood, the two effects must be distinguished. Several methods might be used to separate the variation of glucose concentration from that of albumin. If the wavelength of the radiation reflected at the interface of the blood coincides with the wavelength of a glucose absorption band, the system would be much more sensitive to glucose concentration variations than to those of albumin. The two effects might be distinguished more accurately by using two different wavelengths of radiation, as described in greater detail hereinbelow. Also, albumin has an electric charge of $-18e$ at the pH of blood, and albumin might be removed from the interface where the light strikes by producing an electric field at the interface.

Figure 3A:
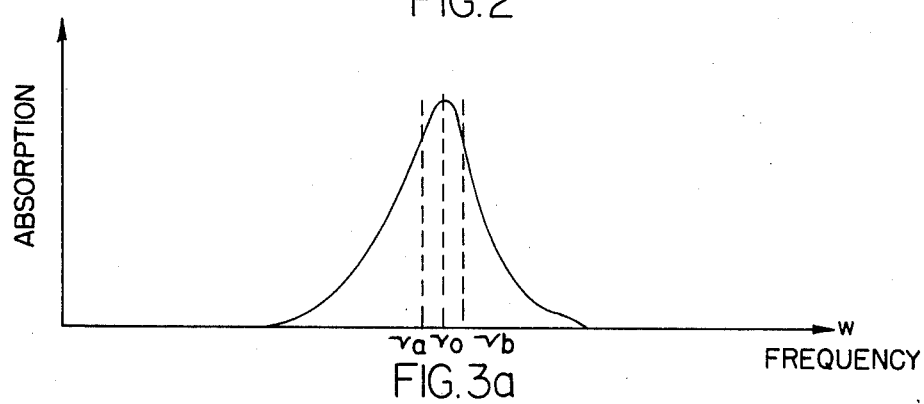
FIG. 3a illustrates a curve of an absorption band as a function of frequency.
Figure 3B:
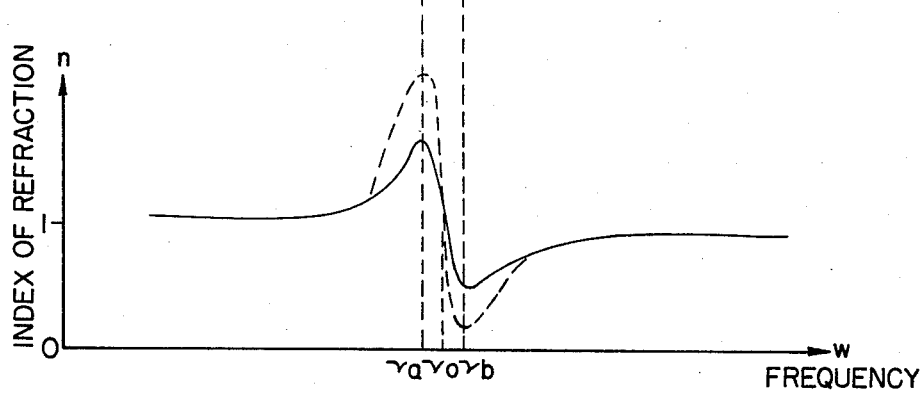
FIG. 3b illustrates a corresponding curve of index of refraction n as a function of frequency, with both figures illustrating the principle of anomalous dispersion at an absorption band for glucose.

FIG. 3a illustrates a curve of an absorption band as a function of frequency $\nu$. FIG. 3b illustrates the corresponding curve of index of refraction n versus frequency. The index of refraction increases at slightly lower frequencies than the center $\nu_o$ of the absorption band and the index of refraction decreases at slightly higher frequencies than $\nu_o$. The index of refraction has an "anomalous" variation at the sides of the absorption band.

Anamalous dispersion occurs at vibrational absorption bands of glucose, which occur in the IR. With operation at a glucose absorption band, as shown in FIG. 3b, the curve of FIG. 3b is altered in intensity in dependence upon the concentration of glucose in the blood, as shown by the dashed curve of FIG. 3b.

This characteristic can be employed to make the measurement specific to glucose only by employing a radiation beam having frequency components at $\nu_a$ and $\nu_b$ and by measuring separately radiation at frequencies $\nu_a$ and $\nu_b$. In this arrangement, a first detector measures the intensity of radiation at $\nu_a$, and a second detector measures the intensity of radiation at $\nu_b$.

If a reading is taken of $$\frac{I_a - I_b}{I_a + I_b} = \text{reading}$$

glucose causes $$I_a - I_b > 0$$

whereas albumin causes both $I_a$ and $I_b$ to change, but $$I_a - I_b = 0.$$

Accordingly, operation of an instrument of this nature at a glucose absorption band allows detection of changes in the index of refraction $n_2$ of blood, while changes in albumin level are discriminated against. In this arrangement, as the glucose level increases, the output $I_a$ of the first detector increases and the output $I_b$ of the second detector decreases in proportion to the increase in glucose level.

Other approaches to discriminating only glucose, and not albumin, could be based upon flow, wherein albumin would be pulled towards the center of the vessel due to fluid dynamic forces related to its density and size compared to other blood constituents and on electrical charge as mentioned hereinabove as albumin has a charge of $-18e$ at the pH of blood.

Figure 4:
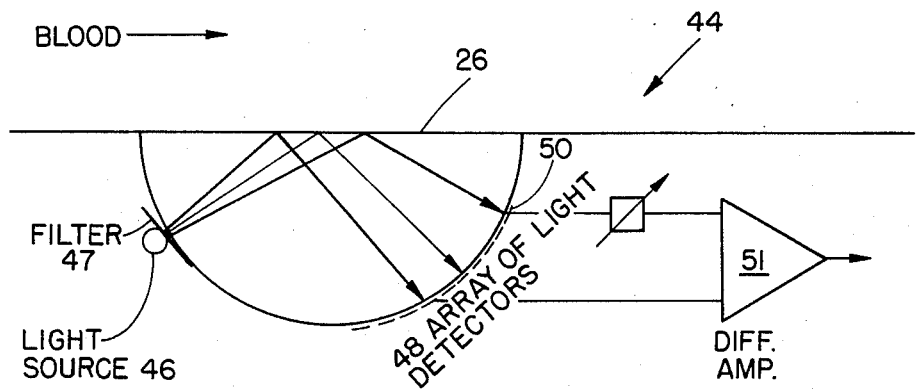
FIG. 4 is a schematic illustration of a first embodiment of an implant showing a principle of operation based upon reflection onto an array of photodetectors.

FIG. 4 is a schematic illustration of a first embodiment of a device 44 showing a principle of operation based upon reflection onto an array of photodetectors. In this arrangement, radiation from a single radiation source 46 such as an LED passes through a filter 47 and illuminates the interface 26 over a range of angles of incidence, each of which is specific to a particular detector in a linear array of detectors 48. Each detector will operate at a different angle of incidence $\theta$ in FIG. 2, and the output signals thereof can be correlated to determine $n_1$. One detector 50 at an angle greater than $\theta_c$ operates with substantially total reflectance to provide a reference signal for every other detector, and each detector in the array employs a separate differential amplifier 51 to provide an output signal.

Figure 5:
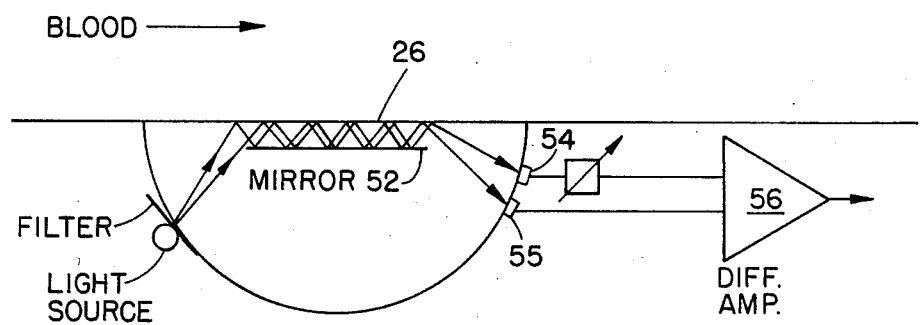
FIG. 5 illustrates an alternative embodiment of an implant designed to perform multiple reflections to enhance the sensitivity and accuracy of the measurement.

FIG. 5 illustrates an alternative embodiment of an implant designed to perform multiple internal reflections to enhance the sensitivity and accuracy of the measurement. In this embodiment, a reflective surface 52 is positioned adjacent to the optical interface, and the beam is directed onto the optical interface at at least two angles near the critical angle. The beam at the first angle will be multiply reflected onto a first detector 54, while the beam at the second angle will be multiply reflected onto a second detector 55, the outputs of which are differentially compared at 56.

Figure 6:
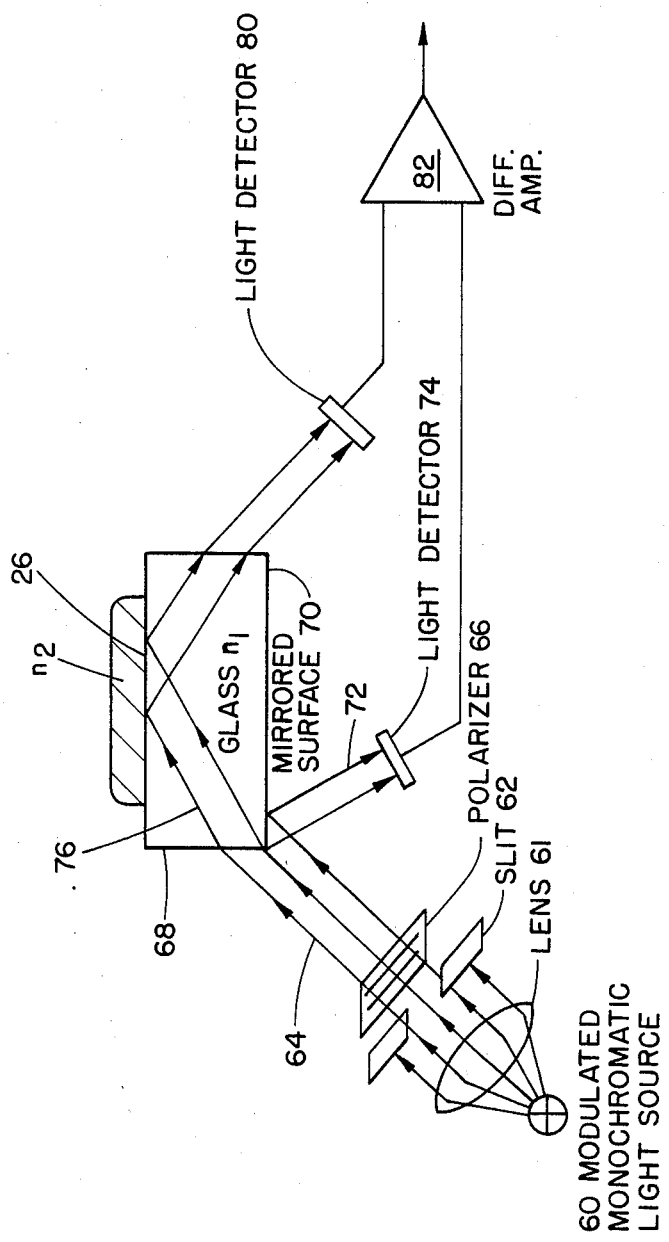
FIG. 6 illustrates a further alternative embodiment of the present invention.

FIG. 6 illustrates a further alternative embodiment of the present invention wherein radiation from a monochromatic light source 60 is collimated by a lens 61 and passes through a slit 62 to form a substantially collimated beam 64 which passes through a polarizer 66 onto a glass optical element 68, which includes a mirrored surface 70 which reflects a reference beam 72 onto a reference detector 74. A portion 76 of the beam 64 is directed against an optical interface 26, and is reflected onto detector 80, and the outputs of detectors 74 and 80 are differentially compared at 82. The beam 64 can be modulated in a manner similar to FIG. 1 to enhance noise rejection by background radiation, etc.

A device pursuant to the teachings of the present invention is designed to directly contact the blood, and the contacting material at the optical interface is preferably constructed of a material with an appropriate critical surface tension, which should be much less susceptible to deterioration by antibodies and proteins. One such exemplary material is dichloro-dimethyl-silane, also known as G.E. Dry Film. The implant is designed to be small and not dissipate much electrical power, and accordingly a light source such as an LED or laser diode is appropriate, and the detector can be constructed of a suitable light sensitive component such as a photodiode or charge coupled device, or an array of charge coupled devices or photodiodes.

Moreover, some embodiments of the present invention can be similar to laboratory instruments rather than implants, in which case miniaturization thereof is not nearly as significant a factor.

The present invention is quite accurate, and allows glucose concentrations to be measured with an accuracy of approximately ±10 mg/dl over a range from about 30 mg/dl to 300 mg/dl, (the normal range in humans is 80-120 mg/dl). By using an instrument with multiple reflections of the polarized light beam therein, even better accuracy should be achievable.

While several embodiments and variations of the present invention for a blood glucose monitor are described in detail herein, it should be apparent that the disclosure and teachings of the present invention will suggest many alternative designs to those skilled in the art.

What is claimed is:

1. A method of measuring the glucose level in blood, comprising:
   a. positioning an optical interface with one surface thereof in direct contact with the blood;
   b. measuring the index of refraction of the blood adjacent to the optical interface by directing a polarized radiation beam at the interface at an angle of incidence slightly less than the critical angle of incidence of the radiation beam relative to the optical interface, and measuring the radiation level of radiation reflected from the interface, which depends upon the index of refraction of the blood adjacent to the interface; and
   c. removing albumin in the blood from the interface to remove the effect of albumin on the index of refraction measurement by applying an electric field to the blood at the interface to remove albumin from the interface.

2. A method of measuring the glucose level in blood as claimed in claim 1, wherein said step of directing a radiation beam includes directing a radiation beam at a wavelength near the wavelength of a glucose absorption band.

3. A method of measuring the glucose level in blood as claimed in claim 1, wherein said step of directing a radiation beam includes directing a radiation beam having two different wavelengths of radiation.

4. A method of measuring the glucose level in blood as claimed in claim 1, including the steps of splitting off a portion of said radiation beam, prior to it being directed at the interface, to form a reference beam, measuring the radiation level of the reference beam, and differentially comparing the measured reference beam with the measured reflected radiation.

5. A method of measuring the glucose level in blood as claimed in claim 1, wherein said step of measuring the reflected radiation is performed with a photodiode.

6. A method of measuring the glucose level in blood as claimed in claim 1, wherein said step of measuring the reflected radiation is performed with an array of photodetectors.

7. A method of measuring the glucose level in blood as claimed in claim 1, wherein said step of directing a radiation beam includes positioning a reflective surface parallel to and adjacent to said optical interface, and directing the radiation beam to perform multiple reflections between the optical interface and the reflective surface.

8. A device for measuring the glucose level in blood, comprising:
   a. said device having an optical interface which is positioned with one surface thereof in direct contact with the blood; and
   b. means for directing a polarized radiation beam at the optical interface at an angle of incidence slightly less than the critical angle of incidence of the radiation beam relative to the optical interface;
   c. means for measuring the radiation level of radiation reflected from the interface, which depends upon the index of refraction of the blood adjacent to the interface and provides a measurement thereof; and
   d. means for removing albumin in the blood from the interface to remove the effect of abuminin on the radiation level measurement, including means for applying an electric field to the blood at the interface to remove albumin from the interface.

9. A device for measuring the glucose level in blood as claimed in claim 8, wherein said means for directing a radiation beam directs a radiation beam at a wavelength near the wavelength of a glucose absorption band.

10. A device for measuring the glucose level in blood as claimed in claim 8, wherein said means for directing a radiation beam directs a radiation beam having two different wavelengths of radiation, and said means for measuring includes a separate measuring means for each different wavelength.

11. A device for measuring the glucose level in blood as claimed in claim 8, including a beam splitter for splitting off a portion of said radiation beam, prior to it being directed at the interface, to form a reference beam, and means for measuring the radiation level of the reference beam, and means for differentially comparing the measured reference beam with the measured reflected radiation.

12. A device for measuring the glucose level in blood as claimed in claim 8, wherein said measuring means includes an array of photodetectors.

13. A device for measuring the glucose level in blood as claimed in claim 8, wherein said means for directing a radiation beam includes a reflective surface positioned parallel to and adjacent to said optical interface, and the radiation beam is directed to perform multiple reflections between the optical interface and the reflective surface.

* * * * *

UNITED STATES PATENT AND TRADEMARK OFFICE
CERTIFICATE OF CORRECTION

PATENT NO. : 4,704,029
DATED : November 3, 1987
INVENTOR(S) : Alan Van Heuvelen

It is certified that error appears in the above-identified patent and that said Letters Patent is hereby corrected as shown below:

Column 4, lines 41 & 47: "$\theta_c = \sin(-1n_2/n_1)$"
should read as -- $\theta_c = \sin^{-1}\frac{n_2}{n_1}$ --

Column 5, line 58: "Anamalous" should read as -- Anomalous --

Signed and Sealed this

Twelfth Day of April, 1988

*Attest:*

DONALD J. QUIGG

*Attesting Officer*      *Commissioner of Patents and Trademarks*